United States Patent [19]

Philippson

[11] 3,966,714

[45] June 29, 1976

[54] PROCESS FOR THE PREPARATION OF A Δ¹-3-KETO STEROID 17-PROPIOLACTONE

[75] Inventor: Rainer Philippson, Bergkamen, Germany

[73] Assignee: Schering Aktiengesellschaft, Berlin & Bergkamen, Germany

[22] Filed: May 23, 1974

[21] Appl. No.: 472,739

[30] Foreign Application Priority Data
May 25, 1973 Germany............................ 2327448

[52] U.S. Cl............................ 260/239.57; 260/397.2; 260/397.4
[51] Int. Cl.²........................ C07J 19/00; C07J 1/00
[58] Field of Search.................... 260/239.57, 397.4

[56] References Cited
UNITED STATES PATENTS

| | | | |
|---|---|---|---|
| 3,325,484 | 6/1967 | Deghenghi.................... | 260/239.55 |
| 3,356,677 | 12/1967 | Beard et al. .................. | 260/239.55 |
| 3,455,909 | 7/1969 | Foell et al..................... | 260/239.55 |
| 3,462,426 | 8/1969 | Baran........................... | 260/239.57 |
| 3,753,979 | 8/1973 | Arth et al. .................... | 260/239.55 |

Primary Examiner—Ethel G. Love
Attorney, Agent, or Firm—Millen, Raptes & White

[57] ABSTRACT

4-Androstene-3,17-dione and 1,4-androstadiene-3,17-dione are converted to 3-(17β-hydroxy-4-androsten-3-on-17α-yl)-propionic acid lactone in three steps by reaction with propargyl alcohol in the presence of an alkali alcoholate of a tertiary alcohol, hydrogenating the thus-produced 17α-(3-hydroxy-propinyl)-17-β-hydroxy compound with hydrogen in the presence of a complex metallic catalyst to produce 17α-(3-hydroxypropyl)-17β-hydroxy-3-keto-androst-4-ene, which is oxidized with chromic acid to the desired lactone.

10 Claims, No Drawings

PROCESS FOR THE PREPARATION OF A Δ⁴-3-KETO STEROID 17-PROPIOLACTONE

BACKGROUND OF THE INVENTION

This invention relates to a process for the production of 3-(17β-hydroxy-4-androsten-3-on-17α-yl)-propionic acid lactone.

Various processes for the preparation of 3-(17β-hydroxy-4-androsten-3-on-17α-yl)-propiolactone are known. Thus, for example, Arth et al., J. Med. Chem. 6 (1963) 617, condense 3β-hydroxy-17-ketoandrost-5-ene with a Grignard reagent from the tetrahydropyranyl ether of propargyl alcohol to obtain the 17α-[3-(2-tetrahydropyranyloxy)-propinyl]-5-androstene-3β,17-diol, which is then hydrogenated to the 17α-[3-(2-tetrahydropyranyloxy)-propyl]-5-androstene-3β,17-diol. After Oppenauer oxidation and subsequent ether splitting, 17α-(3-hydroxypropyl)-4-androsten-17β-ol-3-one is obtained from which, by ring closure reaction with p-tolylsulfonic acid chloride and oxidation by chromic acid/pyridine, the above-mentioned propiolactone is produced.

Another mode of operation is described by Cella et al., J. Org. Chem 24 (1959) 743, also starting with the 3-hydroxy compound. In this process, 3β-hydroxy-5-androsten-17-one is ethinylated, the 17α-ethinyl product is reacted with carbon dioxide to form the 17α-ethinyl-carboxylic acid, which is then reduced with hydrogen to the 17α-ethenyl-carboxylic acid. By acid treatment, the 3-(3β,17β-dihydroxy-5-androsten-17α-yl)-propenoic acid lactone is obtained which is hydrogenated to the saturated lactone, 3-(3β,17β-dihydroxy-5-androsten-17α-yl)-propiolactone. An Oppenauer oxidation follows this reaction, leading to the desired 3-(17β-hydroxy-4-androsten-3-on-17α-yl)-propiolactone.

However, all of these methods have the disadvantage that they involve a rather large number of reaction stages.

The invention is directed to a simpler process for the production of the above-mentioned lactone, starting with 1,4-androstadiene-3,17-dione or 4-androstene-3,17-dione, respectively, requiring a fewer number of reaction stages.

SUMMARY OF THE INVENTION

According to the process of this invention, 3-(17β-hydroxy-4-androsten-3-on-17α-yl)-propionic acid lactone is produced by a. reacting 4-androstene-3,17-dione, 1,4-androstadiene-3,17-dione or a mixture thereof with propargyl alcohol in the presence of an alkali alcoholate of a tertiary alcohol;

b. hydrogenating the thus-produced 17α-(3-hydroxypropinyl)-17β-hydroxy-3-keto-androst-4-ene, androsta-1,4-diene, or mixture thereof, respectively, with hydrogen in the presence of a complex metallic catalyst; and c. oxidizing the thus-produced 17α-(3-hydroxypropyl)-17β-hydroxy-3-keto-4-androstene chromic acid, preferably as a pyridine/chromic acid complex, to produce the desired lactone.

DETAILED DISCUSSION

In the first step of the process, the hydroxypropinyl group is introduced into the 17-position of the starting 4-androstene-3,17-dione or 1,4-androstadiene-3,17-dione. It was surprising that an unsaturated 3,17-diketo steroid of the androstane series could be reacted in such a simple manner with propargyl alcohol in the presence of an alkali alcoholate of a tertiary alcohol, to produce the corresponding unsaturated 17α-(3-hydroxypropinyl)-17β-hydroxysteroids, inasmuch as it was known from the literature that Δ⁴-3-keto steroids isomerize, with potassium tert.-butylate, to the corresponding Δ⁵-3-keto steroids (Tetrahedron Letters 1962, 699). Also, it is known from German Unexamined Laid-open Application DOS No. 2,030,056 that an ethinylation in the 17-position with Δ⁴-3,17-diketo steroids in the 19-nor series in the presence of potassium tert.-butylate can readily be executed without masking the 3-keto group. However, this process cannot be employed with 10-methyl steroids, such as, for example, 18-methyl-4-androstene-3,17-dione, because in case of Δ⁴-3,17-diketo steroids of the 10-methyl series, the 3-keto group must be protected, e.g., by enamination, for example, a pyrrolyl enamine.

The first stage of the process of this invention is suitably conducted by adding the Δ⁴- or Δ¹,⁴-3,17-diketo steroid or mixture thereof, to a solution of the alkali alcoholate of a tertiary alcohol and thereafter introducing the propargyl alcohol.

Suitable reaction solvents are those which are inert with respect to the reactants. Examples are cyclic ethers, e.g., tetrahydrofuran and dioxane, aromatic hydrocarbons, e.g., benzene and xylene, aliphatic ethers, e.g., diethyl ether and glycol dimethyl ether, and polar aprotic solvents, e.g., dimethylformamide and dimethyl sulfoxide.

Suitable alkali alcoholates of tertiary alcohols are, in particular, those which are customarily employed for ethinylation reactions. These alkali alcoholates belong to the generic class of alkali salts of alkanols with 4 to 8 carbon atoms.

Especially suitable alkali alcoholates are the potassium alcoholates, e.g., potassium tert.-butylate and potassium tert.-amylate.

Usually a large molar excess, calculated on the starting steroid, of both the alkali alcoholate and propargyl alcohol, are employed to ensure the reaction goes to completion. For example, about 1 to 12, preferably about 2 to 6 molar equivalents of the alcoholate and about 1 to 10 molar equivalents of propargyl alcohol are employed.

Conventional reaction conditions are employed. Thus, the reaction is advantageously conducted at a temperature below 80° C., preferably from +35° to −20° C. The reaction is usually conducted for at least about 20 min, preferably about 2 to 8 hours, to ensure the reaction has gone to completion.

The reaction product can be worked up in accordance with the usual methods, such as, for example, by precipitation with water or dilute mineral acids, or by concentration under vacuum. The thus-obtained crude product is preferably purified as usual, for example by chromatography or recrystallization, or can be used in the next step without purification.

In the second step of the process of this invention, the thus-produced propinyl grouping in the 17-position is selectively hydrogenated to a 3-hydroxypropyl group under conditions which retain the Δ⁴-3-keto intact, e.g., employing a complex metallic catalyst in a homogeneous phase. By the term complex metallic catalyst is meant a group of hydrogenation catalysts which consists of at least two components: a halide of a metal of Subgroup VIII of the periodic table, e.g. ruthenium and rhodium, and triphenyl phosphine or titanium chloride.

The complex metallic catalyst is preferably provided by tris(triphenyl)phosphine rhodium chloride or tris(triphenyl)-phosphine ruthenium dichloride, which is converted in the presence of hydrogen to the corresponding hydride. Also suitable as catalyst sources are tetrakis(triphenyl)arsine ruthenium chloride or ruthenium-titanium(III) chloride complex.

If the starting compound for the process is 1,4-androstadiene-3,17-dione, the $\Delta^1$-double bond thereof is concomitantly reduced along with the propinyl group, so that the product of the hydrogen stage is the same, whether 4-androstene-3,17-dione, 1,4-androstadiene-3,17-dione, or a mixture thereof is employed as the starting compound.

It is surprising that the multiple bond in the side chain as well as a $\Delta^1$-double bond, when present, is selectively reduced employing these complex metallic catalysts, while the $\Delta^4$-double bond is not concomitantly reduced, since it is known from the literature that tris(triphenyl)phosphine rhodium chloride reduces $\Delta^4$-$\alpha,\beta$-unsaturated 3-keto steroids to the 5$\alpha$-H-compounds. See "Chem. Ber." 101 (1968) 58.

It is also surprising the 17-position propinyl side chain alone is reduced all the way to a propyl side chain, since it would be expected according to the literature that when employing tris(triphenyl)phosphine rhodium chloride the reduction would be arrested at the propenyl group. In the case of ergosta-1,4,22-trien-3-one, the $\Delta^1$-double bond is smoothly reduced, while the $\Delta^{22}$-double bond is not affected (J. Chem. Soc. 1971, 3415).

The second step of the process of this invention is suitably conducted so that the unsaturated 3-keto steroid is hydrogenated in a homogeneous phase, e.g., in an autoclave, in the presence of a complex metal catalyst, preferably tris(triphenyl)phosphine rhodium chloride, usually in an amount of less than 10%, preferably about 0,01 to 5%, by weight based on the steroid to be reduced, when the hydrogenation is conducted under pressure.

The hydrogenation is conducted in the form of a conventional pressure hydrogenation under a pressure of > 1 atmosphere, preferably under pressures of 5–50 atmospheres. Hydrogenation temperatures can range from 0° to 150° C., but preferably the hydrogenation is conducted at 20° to 80° C.

It is possible to effect the hydrogenation without superatmospheric pressure, but in this case the amount of catalyst employed would have to be increased to approximately equimolar quantities.

Suitable solvents are all those which are inert with respect to the reactants. Examples are hydrocarbons, e.g., ligroin and hexane; aromatic hydrocarbons, e.g., benzene or toluene; halogenated hydrocarbons, e.g., methylene chloride or chloroform; ethers, e.g., dioxane or tetrahydrofuran; alcohols, e.g., methanol or ethanol; and ketones, e.g., acetone or methyl isobutyl ketone, and mixtures of these solvents.

In the third step of the process of this invention, the thus-produced 17$\alpha$-(hydroxypropyl)-17$\beta$-hydroxy steroid is oxidized in accordance with conventional methods, employing chromic acid in a suitable reaction medium, e.g., glacial acetic acid or sulfuric acid/acetone or pyridine/menthylene chloride (J. Org. Chem. 35 (1970) 4000), an equivalent strong chemical oxidizing agent, while simultaneously effecting a lactonization to the corresponding $\gamma$-steroido-propiolactone.

The reaction is suitably conducted by gradually adding a solution of 17$\alpha$-(3-hydroxypropyl)-17$\beta$-hydroxy-4-androsten-3-one to a suspension of chromium trioxide in a lower aliphatic hydrocarbon, such as, for example, methylene chloride, and pyridine.

The steroid molecule, except for the conversion of the 17$\alpha$-(3-hydroxypropyl)-17$\beta$-hydroxy group to a propionic acid lactone group, is quite stable to further oxidation. Therefore, a chemical equivalent excess of the chromic acid can be and preferably is employed. In the case of chromic acid/sulfuric acid, only a slight excess, e.g., about 5 to 200% molar excess is required to ensure the oxidation and cyclization reaction goes to completion. With a chromic acid/pyridine complex, a larger excess, e.g., preferably about 3 to 10 fold molar excess is employed.

The oxidation is preferably conducted under mild conditions, e.g., −20° to 60° C., preferably 0° to 30° C. Usually the reaction mixture is maintained at the selected temperature for several hours to ensure the reaction has gone to completion.

The 3-(17$\beta$3-(17$\beta$-hydroxy-4androsten-3-on-3-17$\alpha$-yl)-propiolactone produced according to the process of this invention is itself biologically active (see, e.g., J.Am.Chem.Soc. 79(1957)4808; J.Org.Chem. 24(1959)74; ibid. 24(1959)1109) as well as being an intermediate for the preparation of the known aldosterone antagonist, 3-(7$\alpha$-acetylthio-17$\beta$-hydroxy-3-oxo-4-androsten-17$\alpha$-yl)-propiolactone by dehydrogenation in the 6-position, in accordance with J. Org.Chem. 24(1959)1109, and subsequent reaction with thioacetic acid according to German Published Application DAS No. 1,121,610, for example.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

55 g. of potassium tert.-butylate is combined with 350 ml. of tetrahydrofuran, and 25 g. of 1,4-androstadiene-3,17-dione is dissolved therein. Then, 25 ml. of propargyl alcohol is added dropwise so that the temperature in the reaction vessel does not exceed 25° C., and the mixture is agitated for 5 hours at room temperature. Thereafter, the mixture is neutralized with dilute aqueous sulfuric acid, the thus-formed precipitate is vacuum-filtered, the filtrate is mixed with 100 ml. of water and 200 ml. of methylene chloride, the organic phase is separated and washed twice with respectively 100 ml. of water, dried over sodium sulfate, and evaporated to dryness. The residue is dissolved in benzene and chromatographed over silica gel, thus obtaining 21 g. of 17$\alpha$-(3-hydroxypropinyl)-17$\beta$-hydroxy-1,4-androstadiene-3-one, m.p. 192° C.

EXAMPLE 2

Analogously to Example 1, 22.5 g. of 17$\alpha$-(3-hydroxypropinyl)-17$\beta$-hydroxy-4-androsten-3-one, m.p. 185° C., is obtained from 25 g. of 4-androstene-3,17-dione.

EXAMPLE 3

38 g. of 17α-(3-hydroxypropinyl)-17β-hydroxy-4-androsten-3-one is dissolved in 400 ml. of methanol/benzene 7:3, then 240 mg. of tris(triphenyl)phosphine rhodium chloride is added thereto, and the mixture is hydrogenated in an autoclave at 50° C. and under a pressure of 10 atmospheres hydrogen. The reaction mixture is heated to the boiling point with activated carbon for 30 minutes, filtered, and the carbon additionally washed with a small amount of methanol. By the addition of methanol, the benzene is removed from the filtrate by distillation, and the remaining methanolic solution is stirred into 2 l. of water. The thus-precipitated crude 17α-(3-hydroxypropyl)-17β-hydroxy-4-androsten-3-one is vacuum-filtered, dried, and purified by extraction with isopropyl ether. Yield: 30.1 g., m.p. 167°–168° C. (UV: $\epsilon_{242} = 15,750$).

EXAMPLE 4

Analogously to Example 3, 2.9 g. of 17α-(3-hydroxypropyl)-17β-hydroxy-4-androsten-3-one, m.p. 167°–168° C., is obtained from 4 g. of 17α-(3-hydroxypropinyl)-17β-hydroxy-1,4-androstadien-3-one.

EXAMPLE 5

3.6 g. of chromium trioxide is mixed with 60 ml. of methylene chloride and 6 ml. of pyridine. A solution of 2 g. of 17α-(3-hydroxypropyl)-17β-hydroxy-4-androsten-3-one in 30 ml. of methylene chloride is added dropwise to this suspension, and the reaction mixture is agitated for 24 hours at room temperature under nitrogen. Thereafter, the chromium salts are filtered off, washed with methylene chloride, and the filtrate is washed successively with 5% sodium hydroxide solution, 5% hydrochloric acid, 5% sodium bicarbonate solution, and water. The methylene chloride phase is combined with sodium sulfate and activated carbon and agitated for 30 minutes. Subsequently, the mixture is filtered and concentrated to dryness under reduced pressure. The residue is recrystallized from ethyl acetate, thus obtaining 1.3 g. of 3-(17β-hydroxy-4-androsten-3-on-17α-yl)-propionic acid lactone, m.p. 155°–158° C.

EXAMPLE 6

One gram of 17α-(3-hydroxypropyl)-17β-hydroxy-4-androsten-3-one is dissolved in 80 ml. of acetone and cooled to 5° C. To this solution is added gradually and dropwise such an amount of Jones reagent (solution of 26.72 g. of chromium trioxide in 23 ml. of concentrated sulfuric acid, filled up with water to 100 ml.) that the supernatant solution has a slightly yellow color. The mixture is stirred for 4 hours, then the excess reagent is destroyed with methanol, the thus-precipitated chromium salts are vacuum-filtered, the acetonic solution is concentrated and precipitated in ice water. The 3-(17β-hydroxy-4-androsten-3-on-17α-yl)-propionic acid lactone precipitated by this step is vacuum-filtered, washed neutral with water, and dried, thus obtaining 0.85 g. of 3-(17β-hydroxy-4-androsten-3-on-17α-ol)-propionic acid lactone, m.p. 154.5°–157.5° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of 3(17β-hydroxy-4-androsten-3-on-17α-yl)-propiolactone, which comprises the steps of
   a. reacting 4-androstene-3,17dione, 1,4-androstadiene-3,17-dione, or a mixture thereof, with propargyl alcohol in the presence of an alkali alcoholate of a tertiary alcohol;
   b. selectively hydrogenating the thus-produced 17α-(3-hydroxypropinyl)-17β-hydroxy-3-ketoandrost-4-ene, -androsta-1,4-diene, or mixture thereof, respectively, with hydrogen in the presence as catalyst of a complex of a halide of a metal of subgroup VIII of the periodic table with triphenyl phosphine or titanium chloride; and
   c. oxidizing the thus-produced 17α-(3-hydroxypropyl)-17-hydroxy-3-ketoandrost-4ene with chromic acid.

2. A process according to claim 1 wherein the starting compound is 4-androstene-3,17-dione.

3. A process according to claim 1 wherein in Step (a) the alkali alcoholate is potassium tert.-butylate.

4. A process according to claim 1 wherein in Step (b) the complex metallic catalyst is provided by tris(triphenyl)-phosphine rhodium chloride.

5. A process according to claim 1 wherein in Step (c) the chormic acid is in the form of a acetone-sulfuric acid-chromic acid complex.

6. A process according to claim 1 wherein in Step (a) the alkali alcoholate is potassium tert.-butylate, in Step (b) the complex metallic catalyst is provided by tris(triphenyl)phosphine rhodium chloride, and in Step (c) the chromic acid is in the form of a acetone-sulfuric-acid chromic acid complex.

7. A process for the production of 17α-(3-hydroxypropyl)-17β-hydroxy-4-androsten-3-one which comprises hydrogenating 17α-(3-hydroxypropinyl)-17β-hydroxy-4-androsten-3-one, 17α-(3-hydroxypropinyl)-17β-hydroxy-1,4-androstadiene-3-one, or a mixture thereof, with hydrogen and tris(triphenyl)-phosphine rhodium chloride.

8. A process according to claim 7 wherein the compound which is hydrogenated is 17α-(3-hydroxypropinyl)-17β-hydroxy-4-androstene-3-one.

9. A process according to claim 7 which comprises the step of reacting 4-androstene-3,17-dione, 1,4-androstadiene-3,17-dione, or a mixture thereof, with propargyl alcohol in the presence of an alkali alcoholate of a tertiary alcohol to produce the starting 17α-(3-hydroxypropinyl)17β-hydroxy compound.

10. A process according to claim 9 wherein the starting steroid is 4-androstene-3,17 -dione and the alkali alcoholate is potassium tert.-butylate.

* * * * *